(12) United States Patent
Szeto

(10) Patent No.: US 7,379,770 B2
(45) Date of Patent: May 27, 2008

(54) DEVICES AND METHODS FOR HEART RATE MEASUREMENT AND WRIST-WATCH INCORPORATING SAME

(75) Inventor: Chi Cheong Szeto, Hong Kong SAR (CN)

(73) Assignee: Dayton Technologies Limited, Hong Kong Sar (CN)

( * ) Notice: Subject to any disclaimer, the term of this patent is extended or adjusted under 35 U.S.C. 154(b) by 388 days.

(21) Appl. No.: 10/461,353

(22) Filed: Jun. 16, 2003

(65) Prior Publication Data
US 2004/0228217 A1    Nov. 18, 2004

(30) Foreign Application Priority Data
May 13, 2003    (HK) ................ 03103351.4

(51) Int. Cl.
*A61B 5/0402*    (2006.01)
(52) U.S. Cl. ..................................... 600/519
(58) Field of Classification Search .......... 600/508, 600/509, 519–521, 523
See application file for complete search history.

(56) References Cited

U.S. PATENT DOCUMENTS

| | | | |
|---|---|---|---|
| 4,181,134 A * | 1/1980 | Mason et al. ............ | 600/502 |
| 4,221,223 A * | 9/1980 | Linden ..................... | 600/519 |
| 4,420,000 A * | 12/1983 | Bailey ...................... | 600/519 |
| 4,616,659 A * | 10/1986 | Prezas et al. ............. | 600/519 |
| 4,938,228 A * | 7/1990 | Righter et al. ............ | 600/503 |
| 5,289,824 A | 3/1994 | Mills et al. | |
| 5,351,695 A * | 10/1994 | Mills et al. .............. | 600/508 |
| 5,738,104 A | 4/1998 | Lo et al. | |
| 5,876,350 A | 3/1999 | Lo et al. | |
| 6,418,394 B1 * | 7/2002 | Puolakanaho et al. ...... | 702/139 |
| 6,584,344 B2 * | 6/2003 | Hannula ................... | 600/509 |

FOREIGN PATENT DOCUMENTS

JP    2002306438    10/2002

OTHER PUBLICATIONS

Wang, Boliang et al, "Algorithm for Real-time Detection of QRS Complex in ECG Signal", Space Medicine & Medical Engineering, vol. 8, No. 1, Mar. 1995, pp. 23-26.

* cited by examiner

*Primary Examiner*—Scott M. Getzow
(74) *Attorney, Agent, or Firm*—Buchanan Ingersoll & Rooney PC

(57) ABSTRACT

A method and device for heart rate measurement uses a stream of signals containing ECG signals to select a reference QRS complex according to a set of predetermined criteria and obtain electrical signal characteristics of the reference QRS complex. A first QRS complex is detected from the stream of signals and characterized in relation to the reference QRS in the time domain such that the first QRS complex meets another set of predetermined criteria, and satisfies a level of similarity with the reference QRS complex. An instantaneous heart rate of a subject is evaluated based on the first and the reference QRS complexes when the first and the second QRS complexes are sufficiently similar.

20 Claims, 15 Drawing Sheets

| 1 unit = 3/128 | | $t_1$ | $t_2$ | $t_3$ | $t_4$ | $t_5$ | $t_6$ | $t_7$ | $t_8$ | $t_9$ | $t_{10}$ | $t_{11}$ | $t_{12}$ | $t_{13}$ | $t_{14}$ | $t_{15}$ |
|---|---|---|---|---|---|---|---|---|---|---|---|---|---|---|---|---|
| Reference ECG | $T_{(i)}$ | 1 | -1 | -7 | -13 | -11 | 6 | 30 | 39 | 20 | -12 | -35 | -36 | -17 | 3 | 14 |
| First ECG | $S_{1(i)}$ | 7 | 2 | -5 | -12 | -11 | 1 | 22 | 36 | 26 | -4 | -30 | -31 | -16 | -6 | -3 |
| Second ECG | $S_{2(i)}$ | -6 | 0 | 2 | -1 | -3 | 5 | 20 | 23 | 6 | -15 | -25 | -19 | -6 | 3 | 7 |
| | $N_{1(i)}$ | -2 | -3 | -4 | -9 | -10 | 0 | 13 | 16 | 7 | -2 | -3 | -1 | -1 | -6 | -8 |
| | $N_{2(i)}$ | -30 | -31 | -16 | -6 | -3 | 3 | 14 | 21 | 15 | 5 | -1 | -5 | -7 | -6 | -3 |
| | | | | | | | | | | | | | | | | |
| $\Sigma T_{(i)} * T_{(i)} =$ | 6357 | 1 | 1 | 49 | 169 | 121 | 36 | 900 | 1521 | 400 | 144 | 1225 | 1296 | 289 | 9 | 196 |
| $\Sigma T_{(i)} * S_{1(i)} =$ | 5333 | 7 | -2 | 35 | 156 | 121 | 6 | 660 | 1404 | 520 | 48 | 1050 | 1116 | 272 | -18 | -42 |
| $\Sigma T_{(i)} * S_{2(i)} =$ | 3621 | -6 | 0 | -14 | 13 | 33 | 30 | 600 | 897 | 120 | 180 | 875 | 684 | 102 | 9 | 98 |
| $\Sigma T_{(i)} * N_{1(i)} =$ | 1462 | -2 | 3 | 28 | 117 | 110 | 0 | 390 | 624 | 140 | 24 | 105 | 36 | 17 | -18 | -112 |
| $\Sigma T_{(i)} * N_{2(i)} =$ | 1995 | -30 | 31 | 112 | 78 | 33 | 18 | 420 | 819 | 300 | -60 | 35 | 180 | 119 | -18 | -42 |

*Fig. 12*

DEVICES AND METHODS FOR HEART RATE MEASUREMENT AND WRIST-WATCH INCORPORATING SAME

FIELD OF THE INVENTION

This invention relations to devices, means and methods for heart-rate measurement and, more particularly, to portable or wrist-worn devices for heart-rate measurement and means and methods particularly suitable for such portable devices. More specifically, although of course not solely limited thereto, the present invention relates to a wrist-watch incorporating means for heart-rate measurement.

BACKGROUND OF THE INVENTION

Heart-rate is an important parameter which is indicative of the body conditions of a human being. During exercise, sports or athletic activities, it is always desirable to monitor the heart-rate for optimal results as well as for personal safety. The simplest way to measure heart-rate is probably by finger pressing the wrist and then counting the number of heart beats within a given time in order to calculate the heart beat per minute (BPM). However, such a primitive method may not give an accurate result, requires a relatively long pulse-counting period and may not be sufficiently reliable for most practical purposes. To facilitate more accurate and convenient heart-rate measurements, devices with electrocardiographic (ECG) signal processing and measuring means are available.

ECG signals are electrical signals flowing through the heart which are indicative of the electrical activity of the heart and are usually picked up from the skin. Each typical and complete ECG signal or electrocardiogram includes a complete waveform with the more salient labels P, Q, R, S and T indicating the more distinctive and significant features of the waveform. It is generally recognized that the P wave arises from the depolarisation of the atrium, the QRS complex arises from depolarisation of the ventricles, and the T-wave arises from re-polarization of the ventricle muscle. The magnitude of the tall, spiky R-wave of the PRS complex is approximately 1 mV. When the heart beats, a train of repetitive ECG signals with the characteristic P-QRS-T waveform can be detected. The instantaneous heart-rate can be determined from the period of the train of ECG signals, for example, by measuring the time difference between immediately adjacent spiky R-peaks of the train of the ECG signals.

In order that the heart-rate can be determined by automated ECG analysis for enhanced accuracy, sensitivity, convenience as well as within a shorter time, devices with automated ECG analysis capability are required. ECG signals are usually detected by applying electrodes to the skin, usually also in the presence of noise. Typical examples of noise sources which are commonly known to corrupt ECG signals include, for example, power line interference, electrode contact noise motion artefacts, muscle contraction (electrode myographic, EMG), based line drift and ECG amplitude modulation with respiration, instrumentation noise generated by electronic devices, electrosurgical noise and other, less significant noise sources. The nature and significance of such noise sources have been extensively studied and discussed in many publications, including, for example, in the journal article entitled "A Comparison of the Noise Sensitivity of Nine QRS Detection Algorithms" by G. M. Friesen published in 1990 IEEE Trans-Actions on Biomedical Engineering Vol. 37, No. 1., which is incorporated herein by reference. As the ECG signal data received from the skin are usually contaminated with noise, heart-rate measurement devices equipped with ECG signal analysing means always include noise filtering means or algorithms in addition to ECG signal processing and analysing means or algorithms. Digital signal processing techniques are frequently used to perform noise filtering as well as ECG signal processing and analysis because of the many different types of noise as well as the rather complicated ECG signal waveform. However, conventional noise filtering and ECG signal processing techniques are very complicated and require substantial computational overhead which usually means a rather long computational time as well as a high energy consumption.

As people are becoming more health conscious, the demand for portable heart-rate monitoring or measuring devices or apparatus have significantly increased. A wrist-worn type heart-rate monitor which is usually incorporated as part of a wrist-watch is a good example of such portable heart-rate monitoring or measuring devices. A typical wrist-worn heart-rate monitoring watch usually includes a wrist-strap, a watch casing with a conductive back cover, an ECG sensing electrode mounted on the watch casing and a digital display panel for displaying the time-of-the-day and the heart-rate in BPM. As a wrist-worn heart-rate monitoring watch is usually powered by a single button cell to attain light weight and a compact design, it is highly desirable if the underlying noise filtering and ECG signal processing algorithms or means do not require excessive power consumption to extend battery life. Examples of wrist-worn heart-rate monitoring watches are known, for example, in U.S. Pat. No. 5,289,824 and U.S. Pat. No. 5,738,104. In the wrist-worn heart-rate monitoring watch disclosed in U.S. Pat. No. 5,289,824, the incoming ECG signal data have to pass through five filtering stages before subjecting to a QRS complex detection and validation process in order to determine the heart-rate.

U.S. Pat. No. 5,738,104 also discloses a wrist-worn heart-rate monitoring watch including two stages of digital filtering, namely, a first stage of a low pass filter and a second stage of band-pass filter. The digitally filtered ECG signal data are then subject to an enhancement signal processing block which includes a differentiation step followed by a squaring or absolute value operation and are then subject to the calculation of the moving average. A template-matching or cross-correlation process on the digitally filtered incoming signal data is then performed to compare or cross check against the results of the enhancement signal processing. The resulting digital data are then analysed to determine the users' heart-rate. However, the algorithms utilized in most known wrist-worn type heart-rate monitoring watches are often not sufficiently power- and time-efficient to satisfy's increasingly stringent consumer demands. Hence, it is highly desirable if there can be provided improved ECG signal processing means or algorithms for heart-rate determination with a reasonable accuracy and a reasonable power- and time-overhead. Thus, it will be highly desirable if there can be provided simplified schemes or methods for heart-rate measurements suitable for portable, low-power, applications.

OBJECT OF THE INVENTION

Accordingly, it is an object of the present invention to provide improved or enhanced ECG signal analysing and processing means and algorithms which are particularly useful for portable or wrist-worn devices or apparatus. More specifically, it is an object of the present invention to provide simplified ECG signal processing and analysing means and algorithms for heart-rate determination which are suitable or useful for wrist-worn applications such as for incorporation into a wrist-watch. At a minimum, it is an object of this invention to provide the public with a useful choice of heart-rate determination schemes, means, methods or algorithms as well as wrist-worn devices incorporating same.

SUMMARY OF THE INVENTION

According to the present invention, there is provided a portable heart rate measuring device, such as a wrist watch, including:
  means for receiving a stream of signals containing ECG signals,
  means for selecting a reference QRS complex from said stream of signals according to a first set of predetermined criteria, and characterising the electrical signal characteristics of said reference QRS complex,
  means for detecting and characterising a first QRS complex from said stream of signals which is immediately adjacent to said reference QRS complex in the time domain, fulfils a second set of predetermined criteria, and satisfies a threshold level of similarity with said reference QRS complex,
  means for comparing said first QRS complex with said reference QRS complex and evaluating the similarity between said detected first electrical signal and said reference QRS complex,
  means for evaluating the instantaneous heart rate from said first QRS complex and said reference QRS complex when the similarity between said first QRS complex and said reference QRS complex fulfils a predetermined threshold. Preferably, said device further includes means for confirming the heart rate evaluated by said reference QRS complex and said first QRS complex with reference to heart rate evaluated from a second QRS complex.

According to another aspect of the present invention, there is provided a method of measuring the heart rate of a human being, including the steps of:
  receiving a stream of signals containing QRS complexes,
  selecting a reference QRS complex from said stream of signals according to a first set of predetermined criteria, and characterising the electrical signal characteristics of said reference QRS complex,
  detecting and characterising a first QRS complex from said stream of signals which is immediately adjacent to said reference QRS complex in the time domain, fulfils a second set of predetermined criteria, and satisfies a threshold level of similarity with said reference QRS complex,
  evaluating the instantaneous heart rate from said first QRS complex and said reference QRS complex when the similarity between said first QRS complex and said reference QRS complex fulfils a predetermined threshold.

Preferably, said first set of predetermined criteria for selecting said reference QRS complex includes the occurrence of the maximum signal peak of a predetermined minimum amplitude within a predetermined time from the beginning of receipt of said stream of signals.

Preferably, said predetermined time from the beginning of receipt of said stream of signals within which said peak amplitude must occur being in the region of 1.6 seconds.

Preferably, the characterising of the electrical signal characteristics of said reference QRS complex includes the taking and recording of a plurality of samples of the amplitude of said reference QRS complex at a plurality of sampling times within a predetermined window of time, the boundaries of said predetermined window of time being determined with reference to at least a signal characteristic of said reference QRS complex.

Preferably, the signal characteristic of said reference QRS complex for determining the boundaries of said window of time being the peak amplitude of said reference QRS complex.

Preferably, the characterising of said first QRS complex includes the taking and recording of a plurality of samples of the amplitude of said first QRS complex within a predetermined window of time, the time domain location of said window being determined with reference to said reference QRS complex.

Preferably, the time span of said predetermined window of time being adequate to cover a complete QRS complex.

Preferably, said second set of predetermined criteria includes the occurrence of a signal peak of a predetermined minimum amplitude within a predetermined time frame from said reference QRS complex.

Preferably, said second set of criteria includes the occurrence of the peak of said first QRS complex in the region of 0.25 to 1.5 seconds from the peak of said reference QRS complex.

Preferably, the lower and upper boundaries of said time window from said reference QRS complex being determined respectively by the maximum and minimum possible time periods of normal QRS complexes of normal human beings.

Preferably, said second set of predetermined criteria includes the occurrence of a first signal with a sufficient degree of similarity with said reference QRS complex within a predetermined time frame determined by the maximum and minimum time period of a normal QRS complex of a normal human being.

Preferably, the comparison of similarity between said reference QRS complex and said first QRS complex includes the correlation of the corresponding samples of said reference QRS complex and said first QRS complex.

Preferably, the corresponding samples of said reference QRS complex and said first QRS complex being contained in a predetermined window of time, the centre of said predetermined window of time respectively for characterising said reference QRS complex and said first QRS complex being the amplitude peak of said reference QRS complex and said first QRS complex.

Preferably, the sampling intervals and the width of said windows being the same.

Preferably, said width of said sampling window being in the region of 0.1 seconds.

Preferably, the correlation between the corresponding samples of said reference QRS complex and said first QRS complex includes the summation of the multiplication of the relative amplitudes of said corresponding samples.

Preferably, the detection of said first QRS complex includes the continuous seeking of a signal fulfilling said threshold level of similarity with said reference QRS complex within a predetermined window of time.

Preferably, said method including the step of noise filtering before the characterising of said reference QRS complex.

Preferably, said noise filtering includes the filtering of noise due to AC mains.

Preferably, said noise filtering further includes the filtering of noise common in the detection of QRS complexes.

Preferably, said method further including the detection of a second QRS complex from said stream of signals, said second electrical signal being immediately adjacent either to said reference QRS complex or said first detected electrical signal, said second QRS complex fulfils a third set of predetermined criteria and satisfying a threshold level of similarity with said reference QRS complex.

Preferably, said third set of predetermined criteria includes the occurrence of said second QRS complex within a predetermined time frame from said first QRS complex, said forecast time frame being determined by the heart rate evaluated from said reference QRS complex and said first QRS complex.

Preferably, the boundary of said forecast time frame being symmetrical about the predicted time period evaluated with reference to said evaluated heart rate.

Preferably, said boundary being 12.5% of said predicted time period evaluated from said heart rate.

Preferably, said threshold level of similarity between said second QRS complex and said reference QRS complex being within a predetermined range of said threshold level of similarity between said reference QRS complex and said first QRS complex.

According to the present invention, there is provided A portable heart rate measuring device, including:
  means for receiving a stream of signals containing QRS complexes,
  means for selecting a reference QRS complex from said stream of signals according to a first set of predetermined criteria, and characterising the electrical signal characteristics of said reference QRS complex,
  means for detecting and characterising a first QRS complex from said stream of signals which is immediately adjacent to said reference QRS complex in the time domain, fulfils a second set of predetermined criteria, and satisfies a threshold level of similarity with said reference QRS complex,
  means for comparing said first QRS complex with said reference QRS complex and evaluating the similarity between said detected first electrical signal and said reference QRS complex,
  means for evaluating the instantaneous heart rate from said first QRS complex and said reference QRS complex when the similarity between said first QRS complex and said reference QRS complex fulfils a predetermined threshold.

BRIEF DESCRIPTION OF THE DRAWINGS

Preferred embodiments of the present invention will be explained below by way of examples and with reference to the accompanying drawings, in which:

FIG. 12 is a table showing the sampled values of the ECG signals and noise spikes and the TMC matching calculation.

DETAILED DESCRIPTION OF THE PREFERRED EMBODIMENTS

Figure 1:
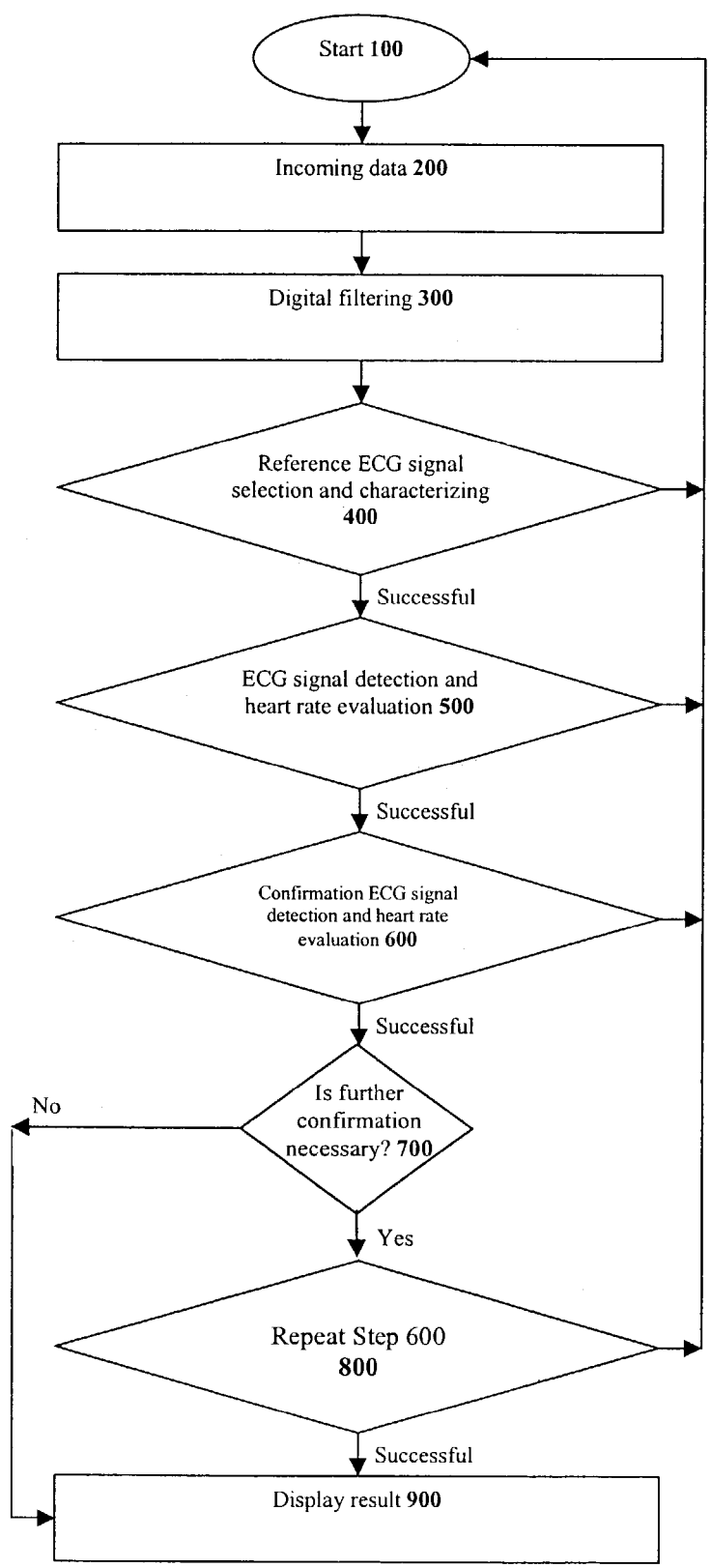
FIG. 1 is a flow chart showing a general overview of a preferred embodiment of a heart-rate measuring algorithm of the present invention.

The electrical activity of the heart is essential to the pumping of blood across the human or other mammals. Such electrical activities of the heart can be picked up by electrodes attached to the body, for example, by attaching electrodes to the skin. The electrical signals thus picked up are commonly referred as ECG signals. A typical ECG signal has a unique waveform which is characterized by the salient feature labels P-QRS-T. While the exact parameters of the ECG waveform may vary from persons to persons, the basic P-QRS-T features are always present in every normal ECG signals. In addition to providing useful information about the conditions of the heart, ECG signals can also be used to evaluate the heart rate, which is usually measured in beats-per-minute (BPM). It is known that normal heart rates are usually within an upper limit and a lower limit. For most practical applications, the lower and upper heart rate limits are respectively 40 and 240 BPM, corresponding respectively to ECG pulse periods of 1.5 seconds and 0.25 second. Of course, heart rate falling outside the aforesaid limits are not unknown.

While the signal characteristics of the ECG waveform may vary between individuals, it is known that the shape of an ECG signal, especially the QRS complex, is substantially similar for a person. Furthermore, while parameters such as the pulse period and peak amplitude of the QRS complexes of a person may vary in the course of time, for example, during exercise or physical activities, such changes are usually gradual, progressive and non-abrupt. In other words, it is noted that ECG waveforms of a person, although constantly varying, is highly predictable.

In an ECG waveform, it is noted that the QRS complex of an ECG pulse is highly definitive of the entire ECG waveform and the tall spiky R peak can be used as a good reference for determining the instantaneous heart rate of a person. For example, the QRS waveform is rather narrow and has a typical time span of between 60 ms and 90 ms. In other words, a QRS complex, or even an ECG pulse, can be adequately or appropriately described or characterized in a small time window of say, 90 to 100 ms, while the period of a normal ECG pulse spans more than, say, 250 ms. Hence, it will be appreciated that heart rate can be determined or evaluated with reference to QRS complexes. In evaluating or determining heart rates with reference to QRS complexes, certain useful characteristics of ECG signals can be utilised.

Firstly, as the normal heart rate is bound by an upper limit and a lower limit, it will follow that no two ECG pulses will occur within a time window which corresponds to a heart rate exceeding the maximum. For example, as the maximum heart rate can be taken as 240 BPM for most practical purposes, no two QRS complexes will occur with a time window of 0.25 second. On the other hand, there must be at least another QRS complex adjacent to an already identified QRS complex within a time window which is equal or larger to the signal period of 1.5 seconds, corresponding to the minimum heart rate of 40 BPM.

Secondly, the analogue nature of the human heart means that the amplitude of the spiky Peak R will not too abruptly change between very adjacent ECG pulses and the amplitudes of adjacent R peaks can be expected to be within a certain range of each other. In other words, the percentage change of the amplitude of immediately adjacent R peaks should be within a certain reasonable range or percentage range, since changes in amplitude of immediately adjacent R peaks will be expected to be gradual and progressive.

Thirdly, the ECG pulse shape or, more specifically, the characteristic Q, R and S features of the QRS complexes, or at least of the adjacent QRS complexes, of a person will show remarkable similarity.

It will become more apparent from the description below that all or a combination of some of the above characteristic features of the QRS complexes can be utilised for heart rate determination for the purpose of the present invention. In this specification, the terms "ECG signal" and "QRS complex" are used interchangeably and will be deemed equivalent whenever appropriate or where the context permits or requires.

From the above, it is noted that the shapes of adjacent QRS complexes of a person bear a certain degree of similarity to each other. Hence, it will be appreciated that the similarity of a pulse with respect to a confirmed or ascertained QRS complex can be a useful criterion for the identification, location or confirmation of another QRS complex.

In the present invention, an ECG pulse will be detected from a stream of signals received from electrodes attached to the body. The QRS complex of this detected ECG pulse will then be used as a reference QRS for identifying, determining and/or ascertaining other QRS complexes for the sake of heart rate evaluation.

For example, the instantaneous heart rate can be determined from the time difference or the separation between two immediately adjacent QRS complexes. This instantaneous heart rate can then be confirmed with reference to another QRS complex or other QRS complexes. That another QRS complex or those other QRS complexes can be a QRS complex or QRS complexes immediately adjacent to those two immediately adjacent QRS complexes upon which the instantaneous heart rate was calculated. It will be noted that the additional QRS complex or complexes can be identified and extracted from a stream of incoming electrical signals by utilising all or a combination of some of the abovementioned characteristic features of QRS complexes, namely, a) heart rate range, b) gradual change of the amplitude of R-peaks of adjacent QRS complexes and, c) similarity of QRS complexes.

Reference QRS Complex

For the sake of simplicity, the reference QRS complex is identified by assuming that a signal peak or a signal with the maximum amplitude which occur within a prescribed time period is a real QRS complex. This assumption is particularly valid in a low-noise ambient environment in which the R-peak of an ECG signal will be the dominant signal during the prescribed period.

As the QRS complex is characterised by a unique spiky peak "R", the signal peak which occurs within a first time window will be assumed to be the R peak. For the examples below, this first time window is set to be 1.6 seconds so that at least an R peak will occur within that period even if a person with the lowest heart rate of 40 BPM (period=1.5 second) for the present purpose is encountered.

Of course, other more sophisticated methods for establishing a reference QRS complex can be used. For example, the characteristics of a reference QRS complex can be downloaded from other sources into the memory of the present application as a reference QRS complex. It will be noted from the description further below that where the ambient environment is noisy, the initially assumed reference QRS complex may be wrong and corrective measures may be taken for rectification.

After the reference QRS complex has been selected, it will be characterised for subsequent use. As the pulse shape of the reference QRS complex is a useful criterion for the determination of other QRS complex, an useful characterisation of the reference QRS complex will be performed by taking the amplitude-time characteristics of the reference QRS complex within a meaningful time period. As mentioned above, the most salient characteristics of a typical QRS complex will appear within a typical characteristic time span of between 60 and 90 ms. Therefore, a sampling window with a width of at least 90 ms will be sufficient to cover most QRS complexes for the present invention. In the present example, a time window of 100 ms for characterising the reference QRS complex is used as a convenient example.

To characterize the reference QRS complex, a plurality of amplitude samples of the reference QRS complex are taken. A sampling frequency of 150 Hz is used as a convenient example in the examples below so that 15 amplitude samples of the reference QRS complex will be taken and recorded within the time window of 100 ms. As the R-peak is between the Q and S features of the QRS complex, the sampling window is set with the signal peak, which is assumed to be the R-peak, being in the center of the time window. Of course, higher sampling frequencies can be used.

The First Detected QRS Complex

After the reference QRS complex has been identified or selected, the next step is to identify a QRS complex which is immediately adjacent the reference QRS complex for heart rate evaluation. From the above, it will be noted that the next QRS complex is expected to be within a time window (W) from the reference QRS complex. More specifically, the next R peak is expected to occur within the time window W from the R peak of the reference QRS complex.

This time window W is defined by a lower time limit $T_1$ and an upper time limit $T_2$, which correspond respectively to the anticipated times of arrival of an R-peak of a QRS complex of the aforesaid maximum and minimum heart rates. In other words, the time difference between the R-peaks of the reference ECG signal and the first detected ECG signal should be at least $T_1$ and at most $T_2$. In the present invention and based on the above-said upper and lower heart rate limits, $T_1$ and $T_2$ are respectively 0.25 second and 1.5 seconds.

Upon fulfilment of the arrival time criterion of the R-peak of the next QRS complex, this target QRS complex will be tested for sufficient waveform similarity with that of the reference QRS complex. In the present example, waveform or pulse shape similarity is compared by performing template matching on two waveforms. An example of a suitable template matching method which can be used to evaluate the similarity of two waveforms is shown in mathematical form below as:

$$TMC = \sum_{i=1}^{15} T(i) \times S(i) \qquad \hat{1}$$

where T(i) is the ith sample value of the reference template signal

S(i) is the ith sample value of the signal being tested.

In this template matching method, pulse shape similarity is evaluated by means of an indicative coefficient, which is designated as the template-matching correlation (TMC). The reference template is built by taking samples of amplitude values of the reference QRS complex within a predetermined time window and at prescribed intervals. In this example, 15 samples of the reference ECG signal are taken within a sampling window of 100 ms at intervals of 6.7 ms with the assumed R-peak being aligned at the centre of the sampling window. Likewise, 15 amplitude samples of the target QRS complex are also taken within the same sampling window of 100 ms at the same intervals for convenience. Of course, different sampling points and/or different sampling intervals may be used without loss of generality. Hence, in the present example, It will be noted that there are equal numbers of samples in the reference template (T(i)) and the target signal (S(i)) to be tested.

The degree of pulse shape similarity is measured or evaluated with reference to a benchmark $TMC_{ref}$ which is set as the self- or auto-correlation of the reference ECG signal itself. In mathematical terms, this is expressed as:

$$TMC_{ref} = \sum_{i=1}^{15} T(i) \times T(i) \qquad \hat{2},$$

where T(i) is the ith sample value of the reference template (reference ECG signal).

Since adjacent QRS complexes of a person are expected to have a high degree of similarity, a real QRS complex will be expected to produce a TMC which exceeds a certain prescribed threshold level. In general, it will be convenient to define the threshold TMC value with reference to the auto-correlation of equation 2. In mathematical terms, this can be represented as:

$$n \; TMC_{ref} \leq TMC \qquad \hat{3}$$

Where n is a threshold constant. Upon empirical trial, it is noted that this threshold constant can be adjusted within a range $n_1$ and $n_2$, where $n_1 \leq n \leq n_2$ for optimal performance to be described below. For example, the threshold constant n can be adapted according to the ambient environment. In this example, the constant $n_2$ and $n_1$ are respectively set as 1.125 and 0.3125 by empirical trial, Of course, other threshold values or limits can be set as and when necessary or where appropriate.

In deciding the appropriate value of the threshold constant n to be used, the following will be considered. If the threshold constant n is set too high, a real QRS complex, for example, a slightly corrupted QRS complex, may be missed. On the other hand, if the threshold constant is set too low, a non-QRS complex with a relatively high peak, for example, a sporadic noise spike, may be taken as a QRS complex. To avoid having to restart calculation all again once the detected QRS complex does not survive the subsequent heart rate confirmation tests, the processor will use a plurality of values of n within the predetermined range for the purpose of equation 3. The calculation may start with $n_1$, the lower limit. If the heart rate calculated from a detected QRS obtained using this lower threshold value survives the heart rate confirmation test, this value is acceptable and can be used for the next confirmatory test. On the other hand, if the confirmatory test fails, the value of n will be incremented and the corresponding threshold TMC value can be retrieved from the memory immediately until the preliminary heart rate can be confirmed, otherwise, re-initialisation will be required.

To identify a QRS complex from a stream or pipeline of incoming data, waveform similarity test is performed on all possible data batches within the appropriate time window in which a valid QRS complex may be present. Due to the serial nature of the incoming data samples, template-matching is continuously and progressively performed on the incoming stream of signal data and whenever a complete batch of samples which may constitute a valid QRS complex has been delivered from the data pipeline and gathered. Thus, this comparison process will be performed on all serial incoming data samples which can correspond to a QRS complex within the time window W of between 0.25 second and 1.5 seconds from the R-peak of the reference QRS complex signal to identify a signal with a TMC falling within the acceptable range as defined above.

As an additional or optional confirmation or assurance, the amplitude of the detected R-peak can be compared with the amplitude of the R-peak of the reference QRS complex. Since the variation of amplitude of immediately adjacent R-peaks should not exceed a reasonable range, the amplitude of the R-peak of the detected ECG should be within an acceptable range of the R-peak of the reference QRS complex. This range of amplitude (R) variation is set as between 40% and 250% of the R-peak of the reference QRS by empirical trial and is given here as a convenient example. In mathematical form, this is expressed as:

$$0.4 R_{ref} \leq R \leq 2.5 R_{ref} \qquad \hat{4}$$

Hence, it will be appreciated that the preliminary heart rate is determined initially from two immediately adjacent QRS complexes, namely, the reference ECG and the first detected ECG, for example, by calculating the time difference between the R-peaks of the respective QRS complexes. To qualify as a real QRS complex, the batch of data representing the tentative QRS complex will have to satisfy the threshold level of TMC.

As an alternative to performing continuous waveform comparison on all possible incoming data batches, QRS complex detection may be done by firstly identifying a data batch which contains the maximum sample (amplitude) value within the prescribed window and then by performing template matching on the data batch. If the resultant TMC exceeds the threshold, this data batch is assumed to be the most adjacent QRS complex. If the TMC test fails, template matching may be conducted on the data batch with the next highest peak sample value and so on.

As another alternative, QRS complex detection may be done by firstly identifying data batches which contain sample (amplitude) data values fulfilling a prescribed condition, for example, the conditions of equation 4. Template matching is then performed on the qualified data batches to identify data batches satisfying the TMC conditions. If there are more than one set of data batches fulfilling the requirements, the first batch in time or the batch with the highest TMC and exceeding the TMC threshold may be taken as the QRS complex. The heart rate derived can then be confirmed with the next QRS complex for correctness. Alternatively, all the qualified QRS complexes may be cross checked with the next, or even the further next, QRS complex for correctness, as to be explained further below.

Confirmation of the Preliminary Heart Rate

After the preliminary heart rate has been determined from the above-mentioned two-QRS-complex-method, the heart rate will be confirmed or tested by checking with another, or a second, QRS complex to obviate or alleviate error.

Similar to the detection of the first QRS complex, this second QRS complex is expected to be within the time window W of between 0.25 second and 1.5 seconds from the first detected QRS complex, or, the reference QRS complex, if the second QRS complex is a QRS complex preceding the reference QRS complex. This second QRS complex can be detected by performing template-matching against the data batches contained in the appropriate window and employing the same of similar set of criteria, although the window will now be shifted. For example, the window W will be measured with reference to the first detected QRS complex where the second QRS complex occurs after the first QRS complex in the time domain.

Hence, the second QRS complex can be detected by performing template matching against the batches of incoming data within the appropriate window W using the reference QRS complex template and subject to satisfaction of the criteria set above for the TMC threshold and amplitude variation.

Since it is unlikely that the heart rate as determined from the immediately adjacent ECG signals can change drastically (at least for the purpose of this invention), the condition that the confirmatory heart rate, as evaluated from this second detected ECG signal, should be within an acceptable range of the preliminary heart rate can be used as a further or alternative confirmation criterion. For brevity, the heart rate which is determined by the reference ECG signal and the first detected heart rate is represented by the symbol $HR_{ref}$ and the additional or alternative confirmatory condition can be expressed in the following terms:

$$k_1 HR_{ref} \leq HR \leq k_2 HR_{ref} \qquad 5$$

In the present example, $k_1$ and $k_2$ are empirically set respectively at 0.875 and 1.125.

As a further confirmation, a third QRS complex signal fulfilling the criteria set with respect to the second QRS complex may further be used to check against the reliability and accuracy of the heart rate thus far calculated. If the heart rate ascertained with reference to the second detected ECG signal does not fulfil the above-said criteria, this suggests possible errors. Consequently, a re-initialisation process to identify a new reference ECG signal and then to evaluate a preliminary heart rate will be re-performed.

Alternatively, the threshold constant n may be increased so that a higher TMC value is adopted for better noise discrimination. If this is employed, the data batch which satisfies the nearest incremented threshold level will be used for calculating the preliminary heart rate to alleviate noise influence before re-initialisation is required.

Hence, it will be appreciated from the above that, heart rate is measured by firstly selecting a reference QRS complex. The selected reference QRS complex is then used as a reference for identifying the nearest QRS complex from an incoming stream of ECG signals. To qualify as a real QRS complex, the QRS complex under test must fulfil a predetermined degree of waveform similarity as well as satisfying all, or a combination of some, of the prescribed anticipated parameters set out above.

The above will now be explained in further detail with reference to a first preferred embodiment as illustrated by the flow charts.

Turning now to the flow chart of FIG. 1, when the heart rate measurement algorithm is actuated by, for example, touching the heart rate sensor of an ECG watch, the heart rate measurement algorithm will start at block 100 and the signal processing means will begin to accept a train of incoming and digitised ECG data. This train of digitised incoming ECG data 200 will be digitally filtered in block 300. This digitally filtered incoming ECG data will be processed to identify a reference ECG signal, or more specifically, the QRS complex, which is then characterized to provide information for the reference template $TMC_{ref}$, as shown in block 400.

After the reference QRS complex has been identified and characterized, the next immediately adjacent QRS complex will be identified as the first detected QRS complex. This first detected QRS complex is immediately adjacent to the reference QRS complex and fulfils a set of predetermined criteria as well as satisfying a threshold level of similarity with a reference QRS complex. The predetermined criteria are more particularly shown in the detailed block 500 of FIG. 4. The criteria, as shown in blocks 502, 504 and 505, include:

a) TMC exceeding a threshold value, as represented by equation 3, b) signal peak amplitude within an anticipated range of the R-peak of the reference QRS complex, as represented by equation 4, and c) occurrence of the R-peak of the expected QRS complex within the time window (W) from the R-peak of the reference QRS complex.

After the most immediately adjacent QRS complex has been identified, the heart rate can be evaluated, for example, from the time difference between the R-peaks of the reference QRS complex and the first detected QRS complex. If no QRS complex satisfying the predetermined criteria can be found, this calibrating or characterising procedure will be started again at 100. If the heart rate is successfully evaluated at block 500, this preliminary heart rate will be confirmed by comparing with a confirmatory heart rate which is to be determined from the next QRS complex. This confirmatory exercise is performed in block 600. As mentioned before, the preliminary heart rate and the confirmatory heart rate should not vary too excessively, otherwise errors are likely to have occurred. If heart rate confirmation fails, the calibrating or characterising procedure will be restarted at block 100. On the other hand, if heart rate confirmation is successful in block 600, the heart rate can be reported for display. Alternatively, an additional confirmatory exercise may be performed for enhanced reliability.

In summary, the predetermined criteria employed in the confirmatory exercise of block 600 of the present example are as follows:

a) TMC exceeding a threshold value, as represented by equation 3, b) a signal peak amplitude within an anticipated range of the R-peak of the immediately adjacent detected QRS complex. In mathematical terms, this is represented by equation 5 as $0.4R_{n-1} \leq R_n \leq 2.5R_{n-1}$, where $R_n$ is the R-peak amplitude of the nth QRS complex which is being tested and $R_{n-1}$ is the R-peak of the immediately adjacent detected QRS complex, c) the occurrence of the R-peak of the expected QRS complex within the time window (W) from the R-peak of the immediately adjacent detected QRS complex, and d) the confirmatory heart rate is within a predetermined range of the reference heart rate $HR_{ref}$, which is the heart rate evaluated from the reference ECG and the first detected QRS complex. In mathematical terms, this is represented by equation 5 as $k_1 HR_{ref} \leq HR \leq k_2$, where $k_1$ and $k_2$ are empirically set respectively at 0.875 and 1.125 in the present invention.

After the evaluated heart rate has been confirmed, the heart rate result can be displayed, for example, by averaging the preliminary and the confirmatory heart rates.

Figure 2:
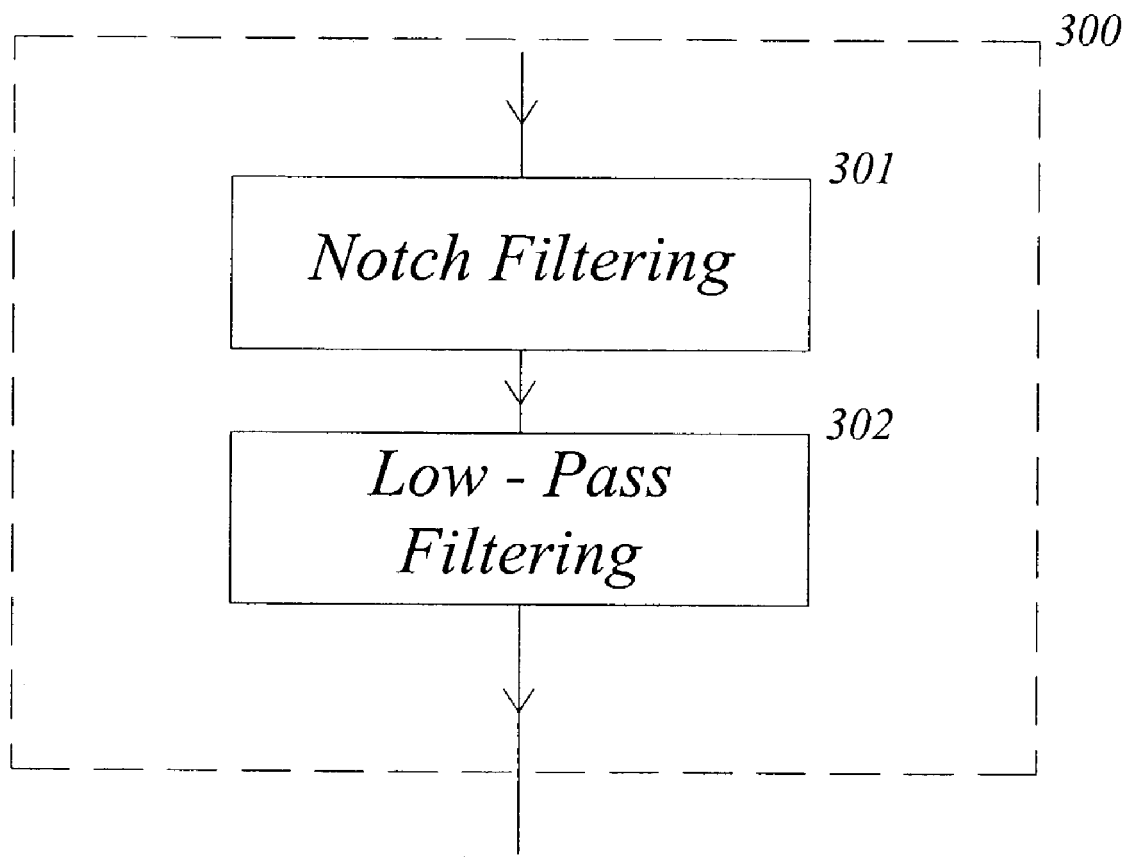
FIG. 2 is a flow chart showing in more detail block 300 of FIG. 1.

Referring to FIG. 2, the digital filtering block 300 includes a notch filtering step 301 and a low-pass filtering 302. Examples of digital filtering schemes suitable for the notch filtering 301 and the low-pass filtering 302 are respectively set out in equations 7̂ and 8̂ below.

Figure 3:
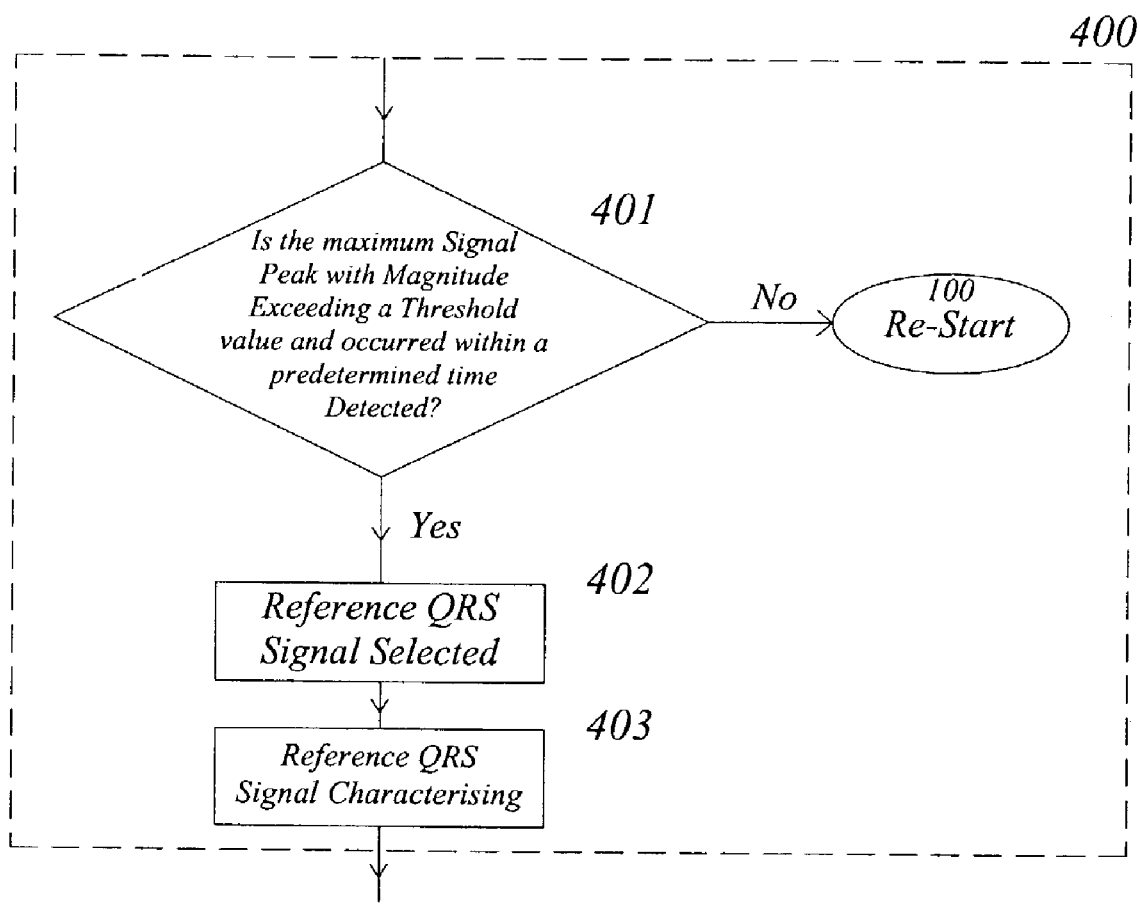
FIG. 3 is a flow chart showing in more detail block 400 of FIG. 1.

FIG. 3 shows in more detail the scheme or method for identifying a reference QRS complex. The reference QRS complex is identified by seeking a maximum signal peak with a magnitude exceeding a threshold value which occurs within a predetermined time (block 401). The prescribed time is set in the present embodiment as 1.6 seconds as a convenient example, since this will cover even the lowest anticipated heart rate of 40 BPM. When the reference QRS complex has been selected (block 402), its waveform will be characterized (block 403) by taking 15 sampling points of its amplitude within a time window of 100 ms. If no reference QRS complex can be identified, the characterising routine will be restarted at 100.

Figure 4:
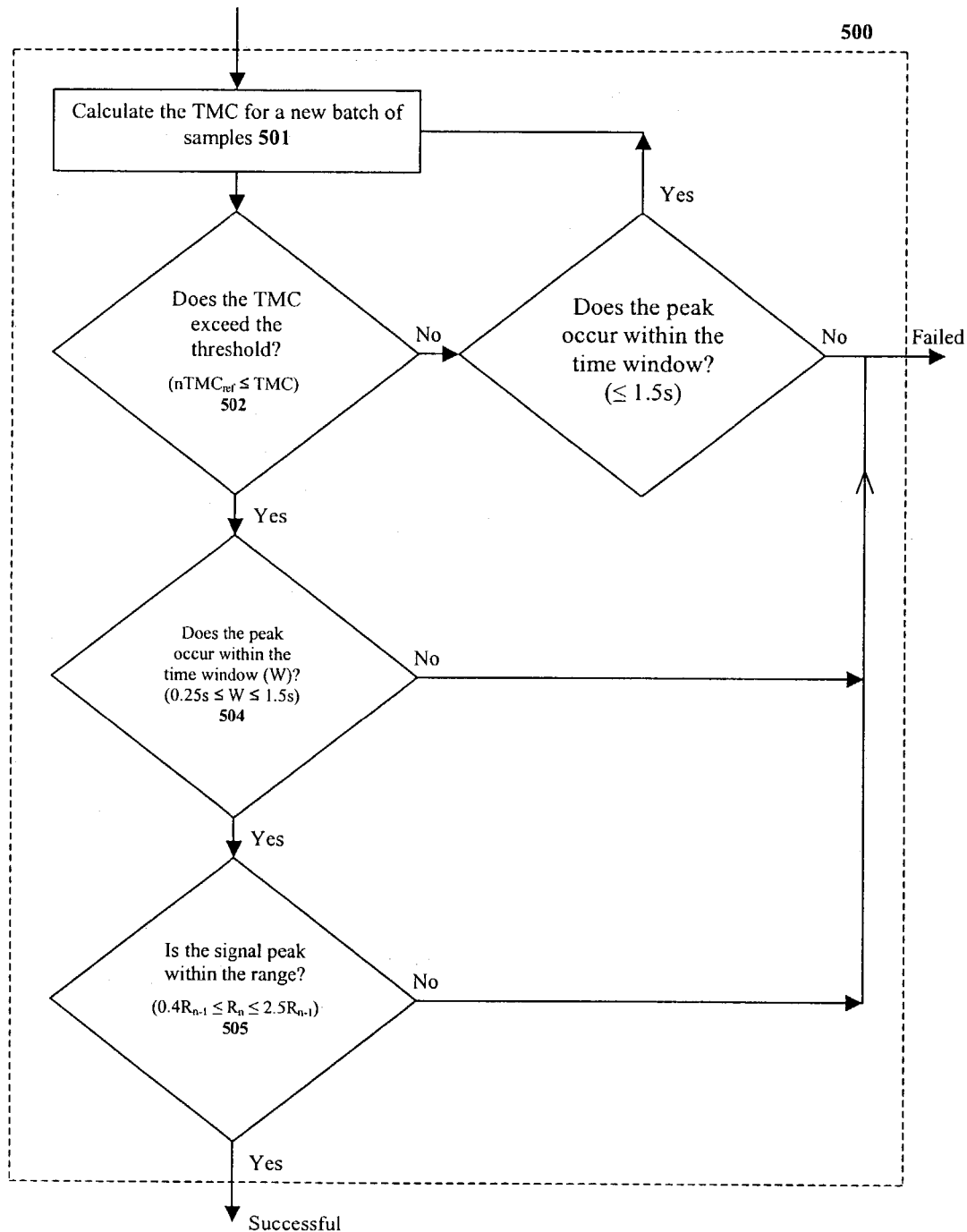
FIG. 4 is a flow chart showing block 500 of FIG. 1 in more detail.
Figure 5:
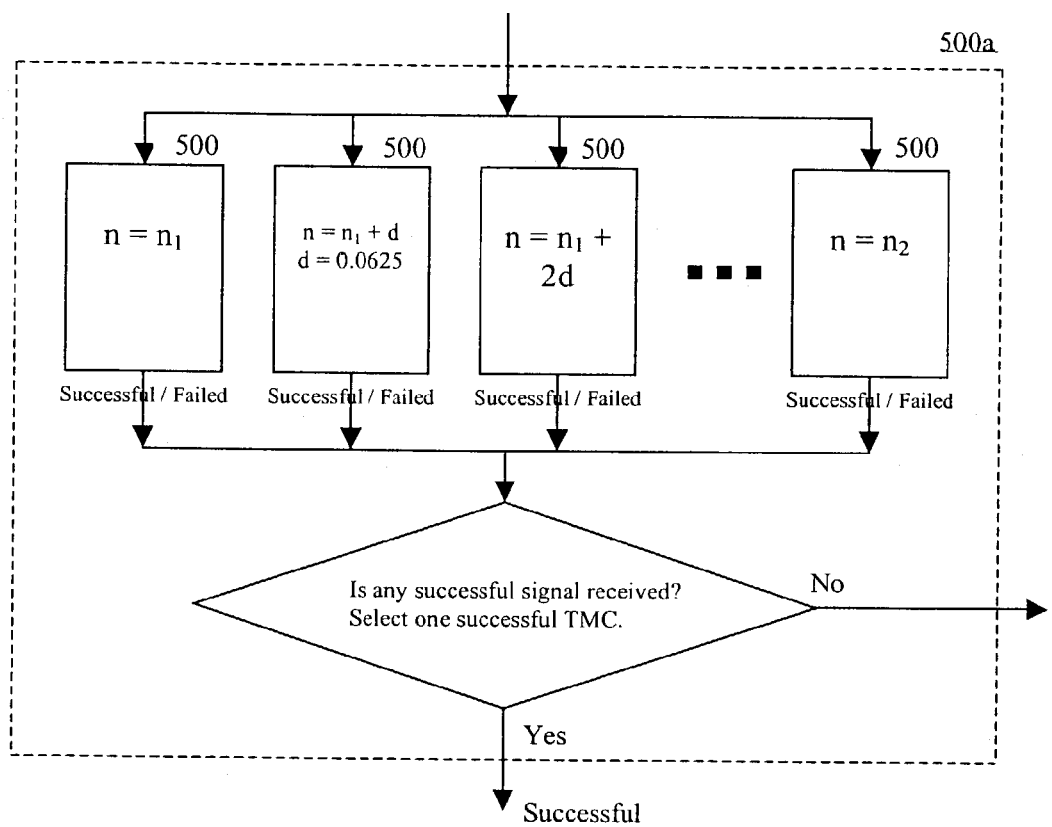
FIG. 5 is a flow chart showing block 500a which can be used in place of the block 500 of FIG. 4.
Figure 6:
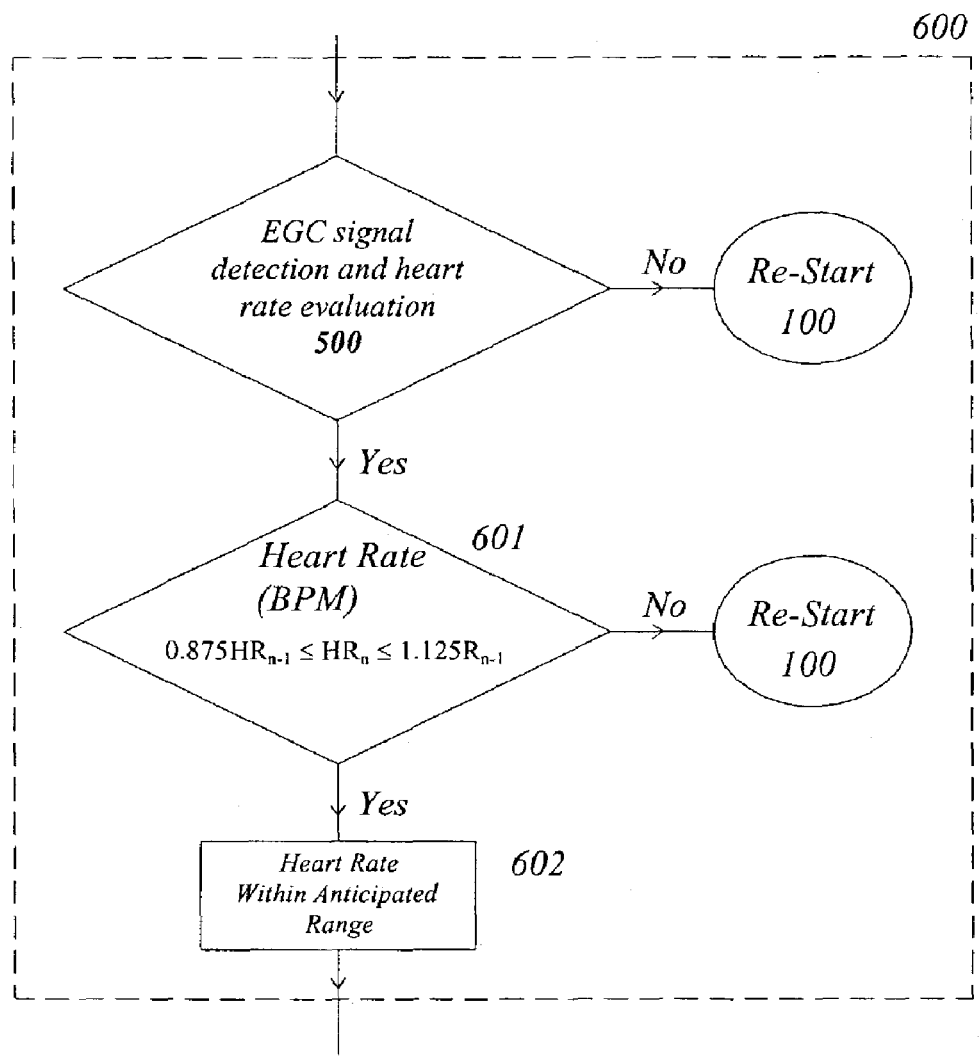
FIG. 6 is a flow chart showing block 600 of FIG. 1 in more detail.
Figure 7:
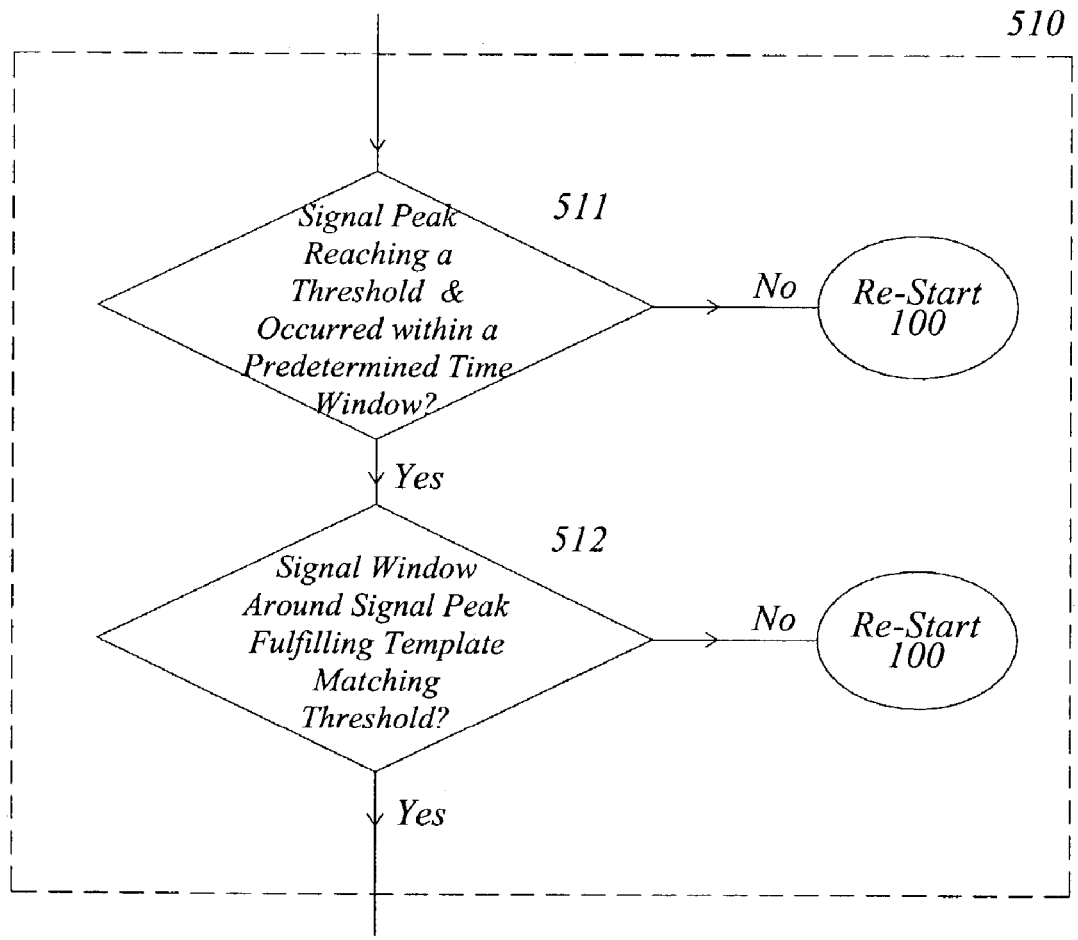
FIG. 7 is a flow chart showing a block 510 as an alternative to block 500 of FIG. 4 for use with the algorithm of FIG. 1.

The scheme 500 for detecting a QRS complex which is immediately adjacent to the reference QRS is shown in more detail in FIG. 4. Referring to FIG. 4, after the reference QRS complex has been identified, the stream of filtered incoming digital ECG signals which have been received and stored will be processed. In this exemplary scheme, TMC calculation 501 will be performed once a batch of 15 data samples which correspond to signal data occurring within the time window W has been received. As mentioned above, this time window W is the time of expected arrival of the next QRS complex with respect to the reference TMC template (obtained from the reference QRS complex). This is a continuous and progressive operation on the stream or pipeline of incoming data so that, for example, when the $16^{th}$ sampled data is received, the TMC of the data batch containing the $2^{nd}$ to the $16^{th}$ sample data will be calculated and compared with the TMC threshold. Likewsie, when the $17^{th}$, $18^{th}$ sample data have been received, TMC of the data batches containing the $3^{rd}$ to the $17^{th}$ samples, the $4^{th}$ to the $18^{th}$ samples and so on of the incoming digital data within the time window W will be calculated and compared with the threshold TMC until a QRS complex satisfying the abovesaid predetermined criteria has been identified. The sample batch producing the acceptable TMC in the time window W will be accepted as a QRS complex.

As an alternative to the continuous processing of all incoming ECG data points, template matching can be performed by firstly identifying a signal peak within the time window of W of between 0.25 second to 1.5 seconds and then to perform the TMC process on the data batch containing that signal peak (e.g., block 511). The calculated TMC value will then be compared with the threshold TMC to determine whether the data batch can be regarded as a QRS complex to reduce computation overhead (e.g., block 512). If the TMC thus calculated does not satisfy the threshold requirement, this process can be repeated on the other lower signal peaks until a lower limit of a reasonable signal peak has been reached. The block 500a shows an alternative scheme describing this alternative scheme which can be used to replace block 500.

After the most adjacent QRS complex has been detected, the heart rate can be evaluated, for example, from the time difference between the adjacent R-peaks of the reference QRS complex and the first detected QRS complex. To confirm that the evaluated heart rate is indeed correct, a confirmatory step 600 will be performed. Further heart rate confirmation, as shown in steps 700 and 800, can be confirmed before the confirmed heart rate is displayed. It will be noted that the process done in the heart rate confirmation step 600 is generally identical to that in step 500 except that an additional constraint 601 is imposed. This additional constraint 601 requires that the confirmatory heart rate evaluated from steps 600 and 800 should not excessively vary from that calculated in step 500. In mathematical terms, this is expressed as:

$k_1 HR_{ref} \leq HR \leq k_2 HR_{ref}$ or, more generally, $$k_1 HR_{n-1} \leq HR_n \leq k_2 HR_{n-1} \qquad \hat{6}$$

where $HR_n$ is the instantaneous confirmatory heart rate and $HR_{n-1}$ is the immediately preceding heart rate.

As mentioned above, in anticipation of possible errors, the constant n for setting the TMC threshold may be varied according to the results of the heart rate confirmation test. To avoid re-calculation after heart rate confirmation has failed, a plurality of n values are used in the alternative calculation block 502a for the calculation of potentially suitable threshold TMCs so that the appropriate stored TMCs may be quickly retrieved for further processing after the heart confirmation test heart failed. Referring to block 500a, the TMC thresholds are calculated by multiplying the reference TMC, ie, $TMC_{ref}$, with a plurality of n values which are between $n_1$ and $n_2$ with a predetermined increment (0.0625 for the present example) between adjacent threshold constants. The resultant TMC thresholds are stored. If the confirmation test fails, a higher TMC threshold will be used until the heart rate confirmation is successful. Otherwise, re-initialisation will be required.

Figure 13:
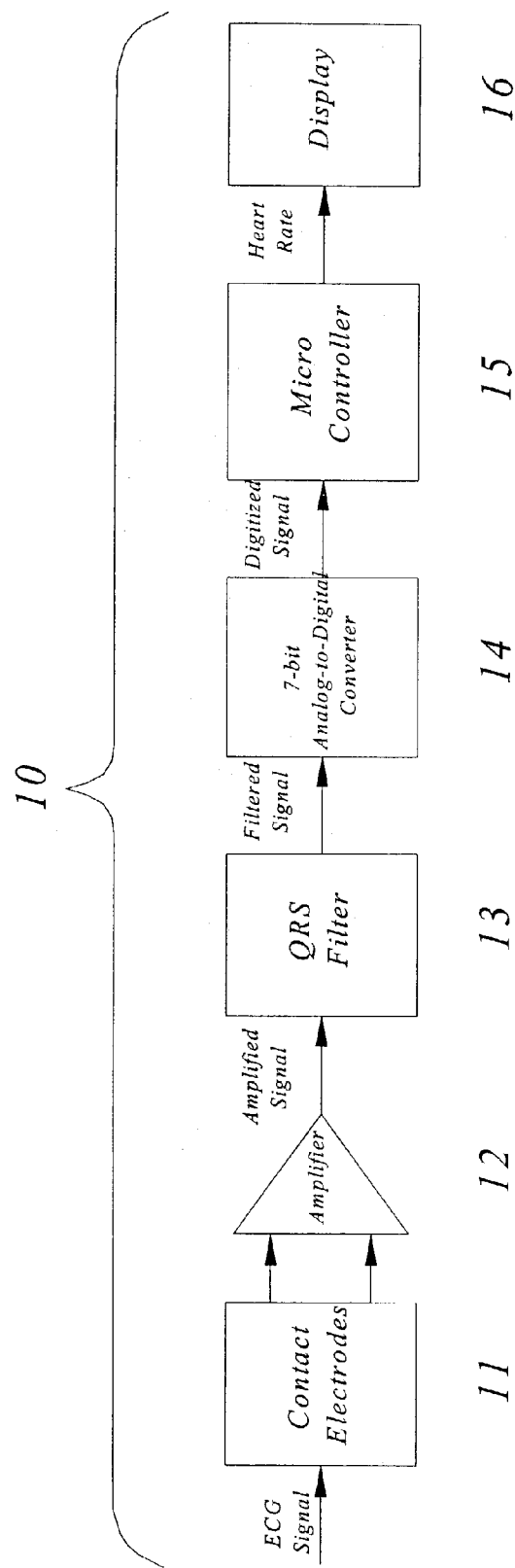
FIG. 13 is a hybrid block and flow diagram showing a preferred embodiment of a wrist-watch type monitoring device incorporating the schemes, methods or algorithms of the present invention.

Referring to FIG. 13, there is shown a block diagram of a preferred embodiment of a heart rate measurement device of the present invention. The device 10 includes contact electrodes 11 for making contact with the skin of a user. The small ECG signals received by the contact electrodes 11 will be fed into an instrumentation amplifier 12, which provides very high input impedance and high common-mode rejection. As the detected ECG signal may contain noise, a band-pass filter 13 with a centre frequency of 17 Hz and a Q of 3 that maximizes the signal-to-noise ratio is connected to the outputs of the instrumentation amplifier. This band-pass filter also serves to match the input range of the analog-to-digital converter as well as serving as an anti-aliasing filter for the analog-to-digital converter.

The amplified and band-pass data are then converted into digital data by an analog-to-digital convertor (ADC) 14. The ADC 14 in this example is a 7-bit ADC operating at a sampling rate of 150 Hz. The digitised incoming ECG signal data are then digitally filtered by a front end digital filter module programmed in the microcontroller 15. In this example, the filters proposed by Engelese and Zeelenberg and referred to in the above Friesen publication is used to enhance the QRS complexes. The Engelese and Zeelenberg filter includes a differentiator with a 62.5 Hz notch filter and a low-pass filter. The signal data received from the ADC first pass through the differentiator with the notch filter, which enhances the slopes of the R-waves and attenuates both the low-frequency noise and the power line signal. Notch frequencies of 60 Hz and 50 Hz are usually used respectively for countries with power line frequencies respectfully of 60 Hz and 50 Hz. In this invention, the difference equation below is used:

$$y0(n)=x(n)-x(n-3) \qquad \hat{7}$$

where x(n) is the nth sample from the analog-to-digital convertor.

y0(n) is the nth output of the differentiator.

Figure 14:
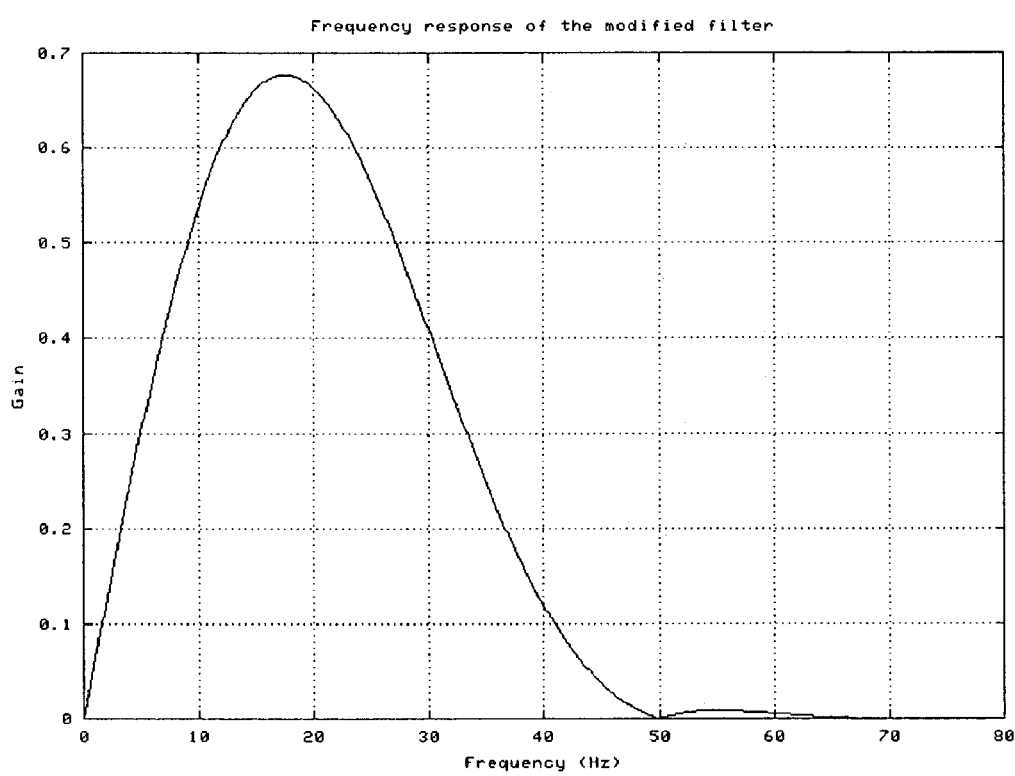
FIG. 14 shows the frequency response of the digital filter used in the present invention.

This difference equation $\hat{7}$ is different from the Engelese and Zeelenberg filter in that (n−3) is used instead of (n−4). A frequency response of this filter is shown in FIG. 14. The input of the differentiator then passes through the low-pass filter, which attenuates the high-frequency noise. The difference equation of the low-pass filter is:

$$y1(n)=y0(n)+4y0(n-1)+6y0(n-2)+4y0(n-3)+y0(n-4) \qquad \hat{8}$$

where y0(n) is the nth sample from the differentiator.

y1(n) is the nth output of the low-pass filter.

The template-matching method as described above is then used to determine the heart rate after the digital filtering has been completed and will be displayed in the display means 16.

Figure 8:
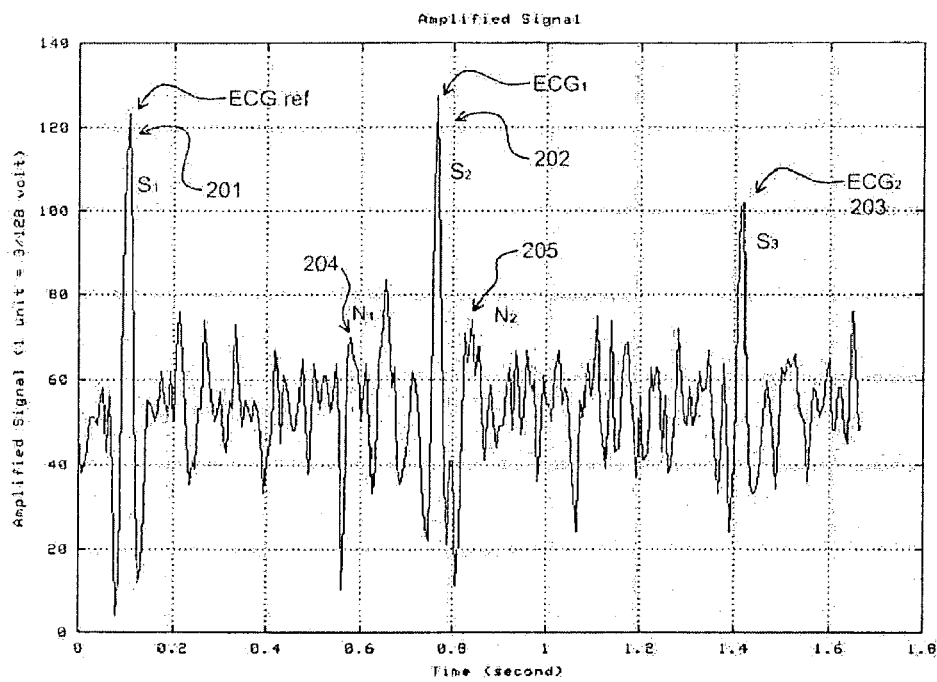
FIG. 8 shows real time ECG signals with three QRS complexes as an example to assist description of the present invention.
Figure 9:
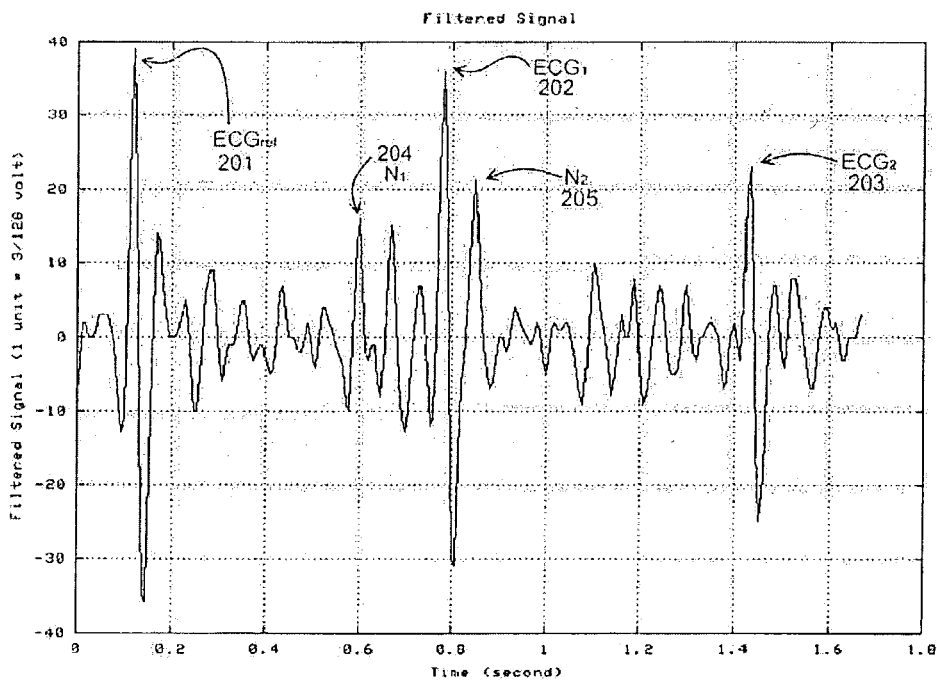
FIG. 9 shows the ECG signals of FIG. 8 after digital filtering according to the algorithm of the present invention.
Figure 10:
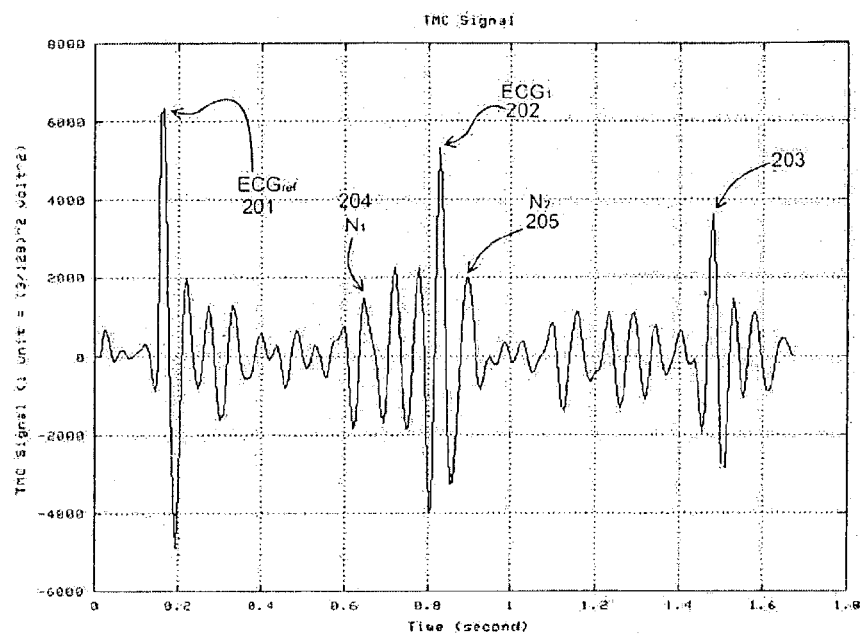
FIG. 10 is a graph showing the template-matching coefficient of the filtered signal of FIG. 9 with respect to the matching template of the reference ECG signal.
Figure 15:
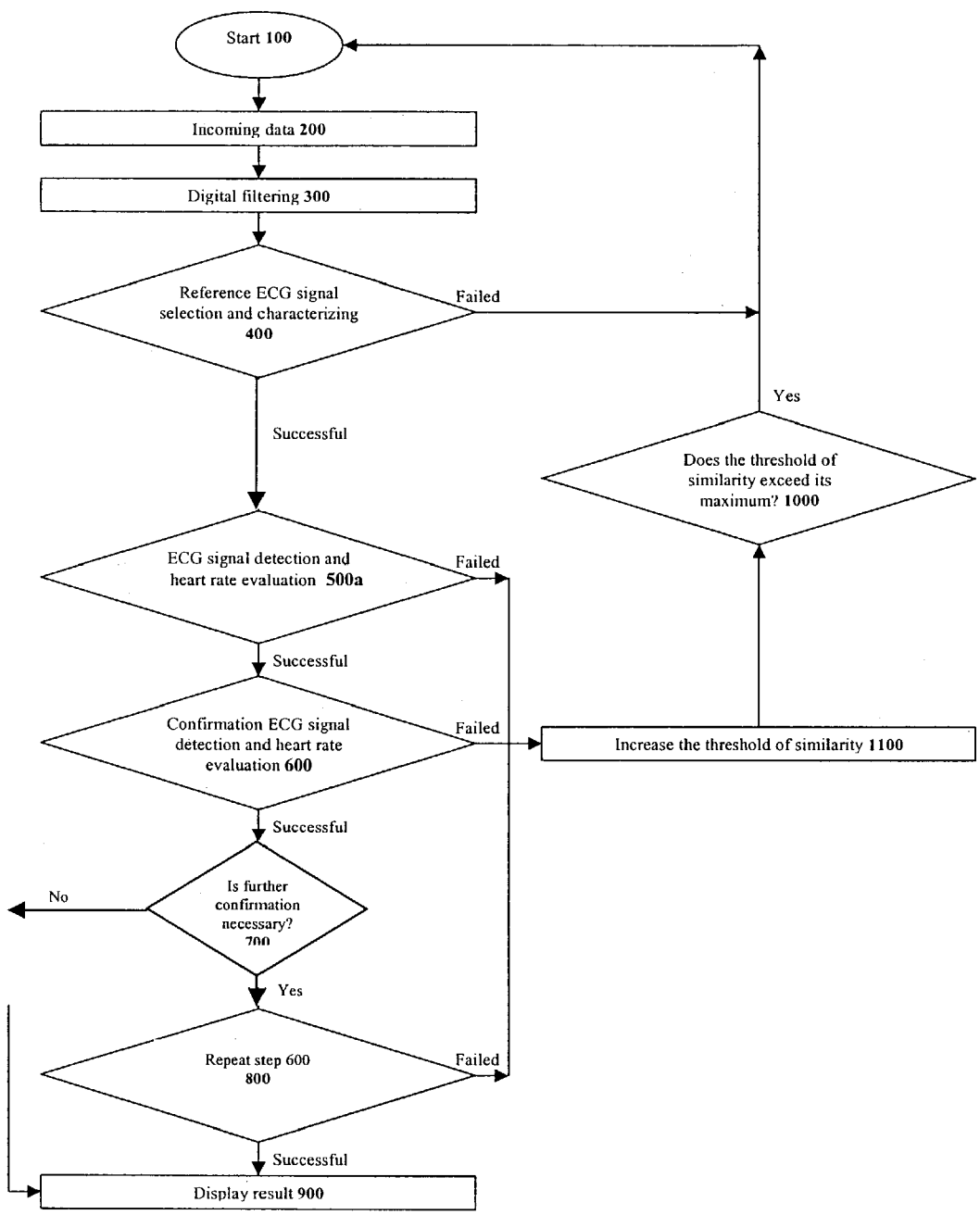
FIG. 15 is a flow chart showing an alternative embodiment of a heart-rate evaluation process of the present invention.

Referring to FIGS. 8-10, there is shown an example train of ECG signals received at the contact electrodes 11 of the sampled preferred embodiment of FIG. 15 and the various subsequent processed signals relevant to the present application.

Referring firstly to FIGS. 8 and 9 corresponding respectively to the ECG signals at the output of the analogue-to-digital converter 14 and the output of the digital filtering block 300, the signals include a reference QRS complex 201, a first QRS complex 202 and a second QRS complex 203. In addition, a first noise spike N1, 204 and a second noise spike N2 205 are also present. 15 sample data are taken within a sample window of 100 ms for all the three QRS complexes and the two noise spikes and the relative values are set out in FIGS. 12a-e. The result of the TMC process, including the various components of the TMC results are set out in more detail in the table of FIG. 12. In particular, it would be noted that the auto-correlation of the reference QRS complex itself has the value of 6357. The TMC between the first QRS complex 202 and the reference QRS complex 201 is 5333 which is 83.9% of the auto-correlation. The TMC between the second QRS complex and the reference QRS complex is 3621 which is 57% of the auto-correlation. On the other hand, the TMCs respectively for the first 204 and the second 205 noise spikes are respectively 1462 (23%) and 1995 (31.4%). As these fall below the threshold TMC, they will be neglected. In the present example, the threshold lower is set at 0.3125 TMC$_{Ref}$ and the threshold upper TMC$_{Ref}$ is 1.125 as mentioned above. In FIG. 10, variation of the TMC values with reference to the filtered signal of FIG. 9 is shown.

To provide enhanced reliability of the heart rate evaluated from the present simplified scheme, the confirmation block 800 can be repeated twice so that a total of four QRS complexes, including the reference QRS complex and three subsequently detected QRS complexes, can be utilised for enhanced reliability. In order to alleviate the possibility of failed detection due to noise, an automated scheme is provided.

Figure 11:
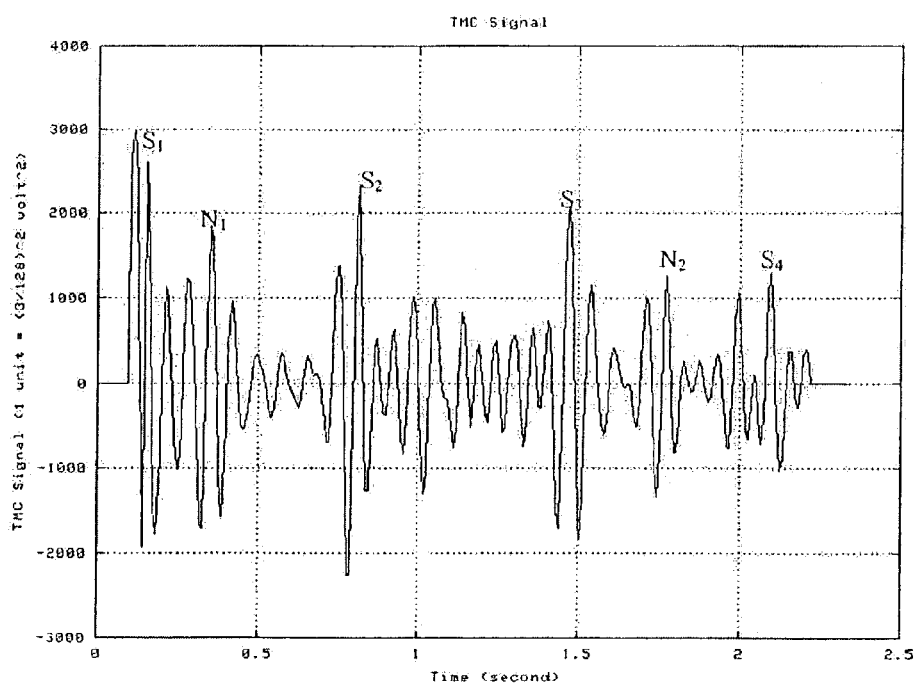
FIG. 11 shows an example of the train of 4 ECG signals (S1-S4) contaminated with a plurality of noise spike (N1-N2)
Figure 12A:
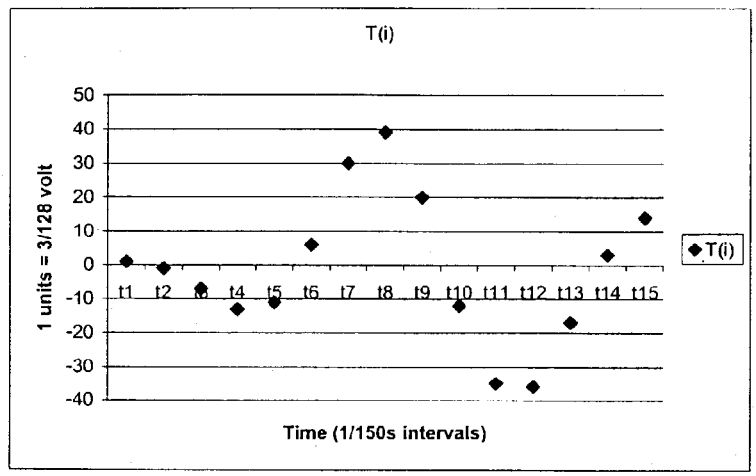
FIGS. 12a-e are graphs showing the data of the individual windows of sampled signals of FIG. 9.
Figure 12B:
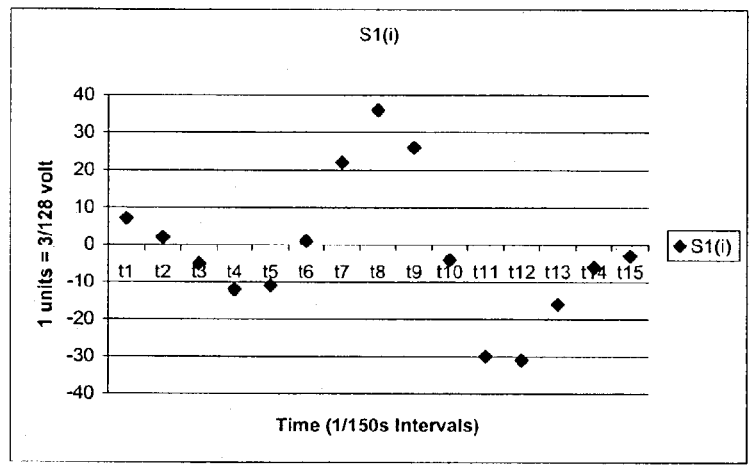
Figure 12C:
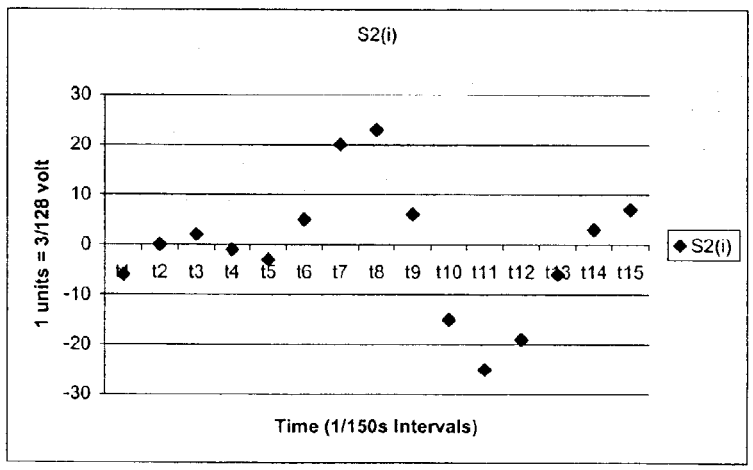
Figure 12D:
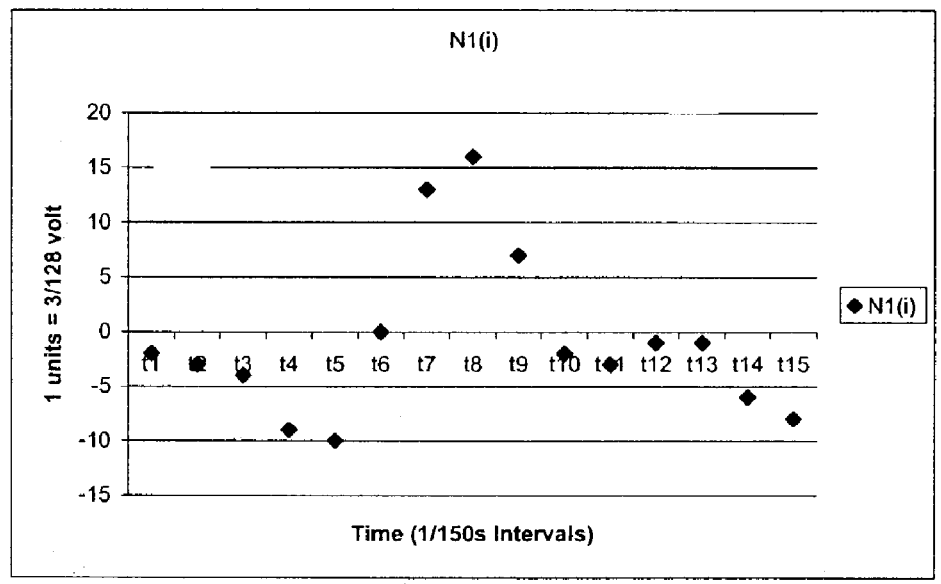
Figure 12E:
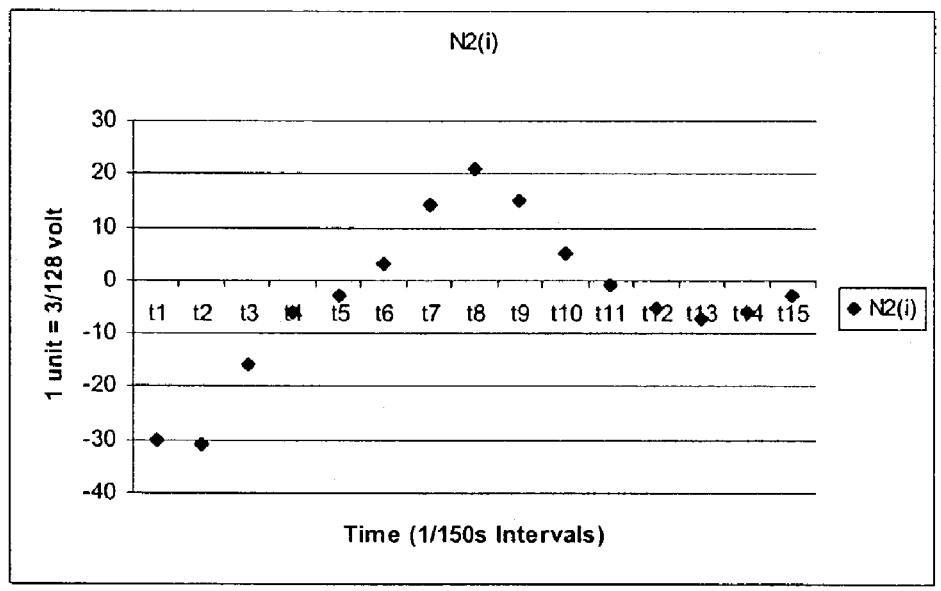

Referring to FIG. 11, there are shown a plurality of QRS complexes with a plurality of noise spikes $N_n$. When the algorithm of FIG. 1 has been successful in detecting the QRS complexes S1, S2 and S3 but failed due to the presence of N1 in advance of the detection of S4, the heart rate calculated with reference to the QRS complexes S1-S3 will be recorded. A re-initialisation procedure will be initiated to seek for the next four continuous QRS complexes. If, again, only three QRS complexes can be detected and the operation failed in advance of the four QRS complexes, it is likely that the ECG measurement is operating in a noisy environment. If this occurs, the heart rate evaluated from the first set of three QRS complexes and the second set of three QRS complexes will be compared. If the two heart rates are comparable, the heart rate, an average of the heart rate with waiting or not, will be displayed as the instantaneous heart rate. This alternative scheme provides additional reliability while not choking the operation of the measurement device in a noisy environment.

FIG. 15 shows a flow chart which is a slightly modified version of the flow chart of FIG. 1 as a second preferred embodiment of this invention. This flow chart is substantially similar to that of FIG. 1 with the alternative block 500a and the exception that, if, in step 600, the confirmation step with reference to the second QRS complex is failed. This may indicate a noisy ambient environment and the first detected QRS complex is in fact noise spike. To alleviate adverse noise influence, the threshold constant n of equation $\hat{3}$ is incremented to increase the hurdle for a signal to be recognised as the first QRS complex in step 500. This step will be repeated until either the second QRS complex is confirmed in step 600 or the threshold constant being used has reached the maximum and there is still no confirmed heart rate.

While the present invention has been explained by reference to the preferred embodiments described above, it will be appreciated that the embodiments are only illustrated as examples to assist understanding of the present invention and are not meant to be restrictive on its scope. In particular, the scope, ambit and spirit of this invention are meant to include the general principles of this invention as inferred or exemplified by the embodiments described above. More particularly, variations or modifications which are obvious or trivial to persons skilled in the art, as well as improvements made on the basis of the present invention, should be considered as falling within the scope and boundary of the present invention.

Furthermore, while the present invention has been explained by reference to a wrist watch with heart rate measurement means, it should be appreciated that the invention can apply, whether with or without modifications, to other portable heart rate measurement means or devices without loss of generality.

The invention claimed is:

1. A method of measuring the heart rate of a human being from a stream of incoming ECG signals, the method including the steps of:

selecting and then characterising a reference QRS complex from said stream of incoming ECG signals;

wherein said reference QRS complex is selected by adopting a local amplitude maximum as the R peak of said reference QRS complex, said local amplitude maximum being present within a predetermined time window and said predetermined time window being a time window within which at least one QRS complex must occur among said stream of incoming ECG signals under normal conditions, and said reference QRS complex is characterised by taking amplitude-time samples of said reference QRS complex;

seeking a first QRS complex from said stream of incoming ECG signals and characterising said first QRS complex by taking amplitude-time samples of said QRS complex for comparison of waveform similarity with said reference QRS complex, said first QRS complex being selected from said incoming ECG signals upon satisfying a first set of criteria of:
  i. satisfying a threshold level of waveform similarity with said reference QRS complex,
  ii. having an amplitude peak within a prescribed range of time from said reference QRS, and
  iii. having its peak amplitude within a prescribed range of the peak amplitude of said reference QRS; and
evaluating a reference heart-rate from said first QRS complex and said reference QRS complex.

2. A method according to claim 1, wherein seeking of said first QRS complex is by the following steps:
seeking a local amplitude maximum in a predetermined time window, said predetermined time window being immediately adjacent said reference QRS complex and being a time window within which a next possible QRS complex may present,
adopting said local amplitude maximum as the R peak of said first QRS complex, and then
comparing waveform similarity between said reference QRS complex and said first QRS complex.

3. A method according to claim 2, wherein the method further comprises additional steps of:
seeking a confirmatory QRS complex after said first QRS complex has been identified, said confirmatory QRS complex satisfying a second set of criteria of:
  i. satisfying a threshold level of waveform similarity with either said reference QRS complex or said first QRS complex,
  ii. having an amplitude peak occurring within a prescribed range of time from either said reference QRS complex or said first QRS complex, and
  iii. having its peak amplitude within a prescribed range the peak amplitude of either said reference QRS complex or said first QRS complex;
evaluating a confirmatory heart-rate from said confirmatory QRS complex, and
confirming a heart-rate for output if the confirmatory heart-rate is within a prescribed range from said reference heart-rate evaluated from said first QRS complex and said reference QRS complex.

4. A method according to claim 3, further comprising the steps of:
incrementing said threshold level of waveform similarity if said confirmatory heart-rate is outside said prescribed range of the reference heart-rate evaluated from said reference QRS complex and first QRS complex,
seeking a new first QRS complex satisfying said first set of criteria with said incremented threshold level and substituting said new first QRS complex for said first QRS complex,
evaluating a new reference heart-rate from said new first QRS complex and said reference QRS,
seeking a new confirmatory QRS complex satisfying said second set of criteria,
evaluating a new confirmatory heart-rate from said new confirmatory QRS complex, and
confirming a heart-rate for output if the confirmatory heart-rate is within a prescribed range from said new reference heart-rate evaluated from said new first QRS complex and said reference QRS complex.

5. A method according to claim 2, wherein the range of variation between said confirmatory heart-rate and said reference heart-rate is 12.5%.

6. A method according to claim 5, wherein said predetermined time window within which at least one QRS must occur under normal conditions is 1.6 seconds.

7. A method according to claim 6, wherein the peak amplitude of said reference QRS complex must occur within said predetermined time window from the beginning of receipt of said stream of ECG signals.

8. A method according to claim 6, wherein the peak amplitude of said reference QRS complex must occur within a time range of 0.25 seconds to 1.5 seconds from the peak amplitude of said reference QRS complex.

9. A method according to claim 8, wherein the peak amplitudes of said reference QRS complex and said first QRS complex is between 40% and 250%.

10. A method according to claim 1, wherein said reference QRS complex is characterised by taking amplitude-time characteristics of said reference QRS complex in a prescribed time span sufficient to characterise said reference QRS complex, said amplitude-time characteristics of said reference QRS complex being for forming a reference matching template.

11. A method according to claim 10, wherein said prescribed time span is at least 90 ms, and preferably 100 ms.

12. A method according to claim 11, wherein the amplitude peak of said local amplitude maximum occurring within said predetermined time window is assumed to be the peak of an R spike of a QRS complex.

13. A method according to claim 10, wherein waveform similarity between said reference QRS complex and said first QRS complex is evaluated by template matching between said reference QRS complex and said first QRS complex, said template matching being performed by comparing said first QRS complex with reference to a reference template, said reference template being formed from amplitude-time characteristics of said reference QRS complex.

14. A method according to claim 13, wherein the degree of waveform similarity between said reference QRS complex and said first QRS complex is measured with reference to a reference benchmark, said reference benchmark being self-correlation or auto-correlation of said reference QRS complex.

15. A method according to claim 14, wherein said reference benchmark is $TMC_{ref}$, wherein $TMC_{ref} = \Sigma_{i-1} T(i) \times T(i)$, n is the number of samples and $T(i)$ is the $i^{th}$ sample value of the reference QRS complex.

16. A method according to claim 15, wherein the degree of waveform similarity is measured by comparing a template matching coefficient TMC with $TMC_{ref}$, wherein $TMC = \Sigma_{i-1} T(i) \times S(i)$, wherein $T(i)$ is the the $i^{th}$ sample value of the reference QRS complex and $S(i)$ is the sample value of the signal being evaluated.

17. A method according to claim 10, wherein amplitude-time samples of said stream of incoming ECG signals are taken serially at regular intervals, and waveform similarity is performed continuously and progressively with said incoming data samples until a set of data samples satisfying said first set of criteria is found within said predetermined time window.

18. An apparatus for measuring the heart-rate of a human being, the apparatus comprising:

- means for receiving, sampling and storing a stream of incoming ECG signals,
- means for detecting a local amplitude maximum from stored samples of said stream of incoming ECG signals within a predetermined time window,
- means for forming a reference QRS template using said local amplitude maximum as an R peak of said reference QRS complex,
- means for seeking a first QRS complex from said stream of incoming ECG signals, said first QRS complex satisfying a first set of criteria of:
  i. satisfying a threshold level of waveform similarity with said reference QRS complex,
  ii. having an amplitude peak occurring within a prescribed range of time from said reference QRS, and
  iii. having its peak amplitude occurring within a prescribed range of the peak amplitude of said reference QRS; and
- means for evaluating a reference heart-rate from said first QRS complex and said reference QRS complex.

19. An apparatus according to claim 18, further comprising a means for seeking a confirmatory QRS complex from said stored sample of said stream of ECG signals, means for evaluating a confirmatory heart-rate from said confirmatory QRS complex, and means to reinitialise seeking of a new reference QRS if said confirmatory heart-rate exceeds a normal range of said reference heart-rate.

20. A wrist watch comprising an apparatus according to claim 18, said wrist watch further comprising:

- an amplifier for amplifying incoming ECG signals,
- a QRS filter for band-filtering said ECT signals,
- an analogue-to-digital converter for converting the band-filtered ECG signals into digital data, and
- a visual display unit for displaying heart-rate information obtained from said ECG signals.

* * * * *